United States Patent [19]

McRae

[11] Patent Number: Plant 6,208

[45] Date of Patent: Jun. 21, 1988

[54] HYBRID ASIATIC LILY NAMED DAYDREAM

[75] Inventor: Edward A. McRae, Boring, Oreg.

[73] Assignee: Melridge Inc., Gresham, Oreg.

[21] Appl. No.: 862,248

[22] Filed: May 12, 1986

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new variety of hybrid lily plant characterized by bearing large clusters of flowers having a cream/peach-pink bicolor pattern, and a complete lack of any spotting, the flowers being of medium size with excellent form and long persistence, both on the plant and as cut flowers. This combination is believed to be completely new in the upright Asiatic division of lilies suited to forcing and to mass commercial cultivation. The plant has a height of about 90 to 100 cm. with a vigorous, upright growth habit and abundant foliage. The plant is highly resistant to disease and shows high tolerance of virus, which makes it an excellent garden plant. The bulbs may be precooled and forced for cut flower production producing clones each of which is vigorous and a good grower and propagator.

1 Drawing Sheet

BACKGROUND OF THE INVENTION

This new variety of lily plant originated as a seedling selected by me from a group of seedlings planted at Sandy, Oreg., in the course of breeding efforts carried on by me with the object of producing spotless upright Asiatic lilies in a variety of pastel colors and well suited to forcing for out-of-season cut flower production, a variety heretofore unknown in the lily breeding art.

The seedlings from which this variety originated resulted from my crossing the clonal cultivar 'Connecticut Queen' as the seed parent and the clonal cultivar 'Sunrise' as the pollen parent, both unpatented varieties.

This particular plant was selected by me for asexual reproduction because it appeared to fulfill the purpose of my breeding efforts and was reproduced by me and under my direction at Sandy, Oreg., by bulb scale propagation with very pleasing results, and for that reason, successive generations of this plant, produced by bulb scale propagation and by natural propagation from bulblets, demonstrated that the novel and distinctive characteristics of this new variety are fixed and hold true under asexual propagation from generation to generation.

DESCRIPTION OF THE DRAWING

My new variety of lily plant is illustrated by the accompanying photographic drawing, which shows a face view of a fully opened bloom in full color and illustrates the flower form and tepal arrangement and, in particular, the distinctive bicolored cream yellow and peach-pink spotless flowers.

DESCRIPTION OF THE NEW VARIETY

The following is a detailed description of my new variety of Asiatic hybrid lily with nomenclature according to The International Lily Register of The Royal Horticultural Society of London (Second Edition, 1969), and with color designations according to The R.H.S. Colour Chart (1966).

THE PLANT

Origin: Seedling.

Parentage:

*Seed parent.*—Lilium 'Connecticut Queen' (unpatented).

*Pollen parent.*—Lilium 'Sunrise' (unpatented).

Classification:

*Horticultural.*—Upright Asiatic Hybrid Lily, Division I-A of The Horticultural Classification of Lilies by The Royal Horticultural Society.

*Commercial.*—Asiatic Lily Cultivar.

Form: Single stem, erect and stately.

Height: About 90 to 100 cm. from bulbs of about 15 to 18 cm. in circumference.

Growth: Vigorous and upright.

Foliage:

*Quantity.*—Abundant.

*Leaf size.*—About 8 to 10 cm. long and about 0.7 cm. wide.

*Leaf shape.*—Lanceolate with acuminate tip.

*Texture.*—Leathery and glossy.

*Color.*—Medium green and somewhat lighter on the under side.

Bulbs:

*Size.*—Various, depending upon age, ranging to about 25 cm. in circumference in commercial use.

*Color.*—White.

THE BUD

Form: Substantially linear with obtuse apex.

Size: About 8 to 9 cm. long and about 5 cm. in circumference just prior to opening.

Opening rate: The bud opens slowly, in response to morning light, opening taking about one hour.

Color: Yellow green, 154C-D, underlayed with 18B at the base and shading to 36B at the tip.

Peduncle:

*Length.*—Averages about 4 to 6 cm., but may become longer if light levels are too low.

*Color.*—Medium green with light plum overlay.

THE FLOWER

Blooming habit: Annually, once and profusely in mid-season for Asiatic lilies.

Size: Medium, for Asiatic hybrids, averaging about 12 to 14 cm. in diameter.

Borne: In a single racemic manner having about 8 to 10 buds from a bulb about 18 cm. in circumference.

Shape: Cup-shaped when bloom first opens and becoming flattened as the tepals recurve during the second day.

Tepalage:

*Number.*—Six.

*Arrangement.*—Hexagonal and imbricated.

*Shape.*—Ovate with entire margins and acuminate tip.

*Appearance.*—Shiny.

*Color.*—The center of the tepals adjacent the base is yellow, 8A, with the color extending about 2 cm. into the tepal body where it is then overlaid with a soft pink pigmentation which deepens as it extends to the tips of the tepals. The pink color, overlaying the creamy yellow, creates a peach-pink visual effect and at the tepal tips the color becomes red, 38B.

*Tepal spotting.*—The tepals are entirely unspotted.

*Color changes.*—The flowers of this variety become slightly lighter as they age. Low light levels and extreme heat may cause the pink pigmentation to decrease.

Pedicel:

*Length.*—About 8 cm. long, in average.

*Form.*—Sturdy and ascending to about 45° from the horizontal.

*Color.*—Medium green with light plum overlay.

Persistence: The tepals stay on the stem about three weeks.

Fragrance: None.

Disease resistance: The flower and plant are resistant to diseases and particularly to Fusarium Bulb Rot and Botrytis Blight, as observed in western Oregon.

Lasting quality: The flower is long lasting, both on the plant and as a cut flower.

REPRODUCTIVE ORGANS

Stamens:

*Number.*—Six.

*Arrangement.*—Typical of the genus Lilium.

Anthers and pollen: Greyed orange, 167A.

Filaments:

*Length.*—About 5 cm.

*Color.*—Soft yellow, 6D.

Pistils:

*Number.*—One.

Style:

*Length.*—About 5 cm.

Stigma: Small and soft green in color.

Character of ovary: Typical of genus Lilium.

THE FRUIT

Fertility: The fruit is fertile.

Shape: Ovoid.

Color at maturity: Soft brown, sometimes overlaid with soft plum.

This new variety of Asiatic hybrid lily most nearly resembles 'Connecticut Queen' but it has a richer yellow in the center of the tepals and a rich peach-pink suffusion reaching almost to the tepal tips. Unlike 'Connecticut Queen', this new variety is quite reliable for forcing out-of-season.

I claim:

1. A new and distinct variety of Asiatic hybrid lily, substantially as herein shown and described, particularly characterized by its unique color pattern of cream yellow throat and peach-pink body and its complete lack of spots, and the excellent of its flower form; this plant has a vigorous growth habit and rapid natural propagation; and it has excellent versatility both as a garden plant and as a cut flower producer from precooled bulbs forced out-of-season under glass.

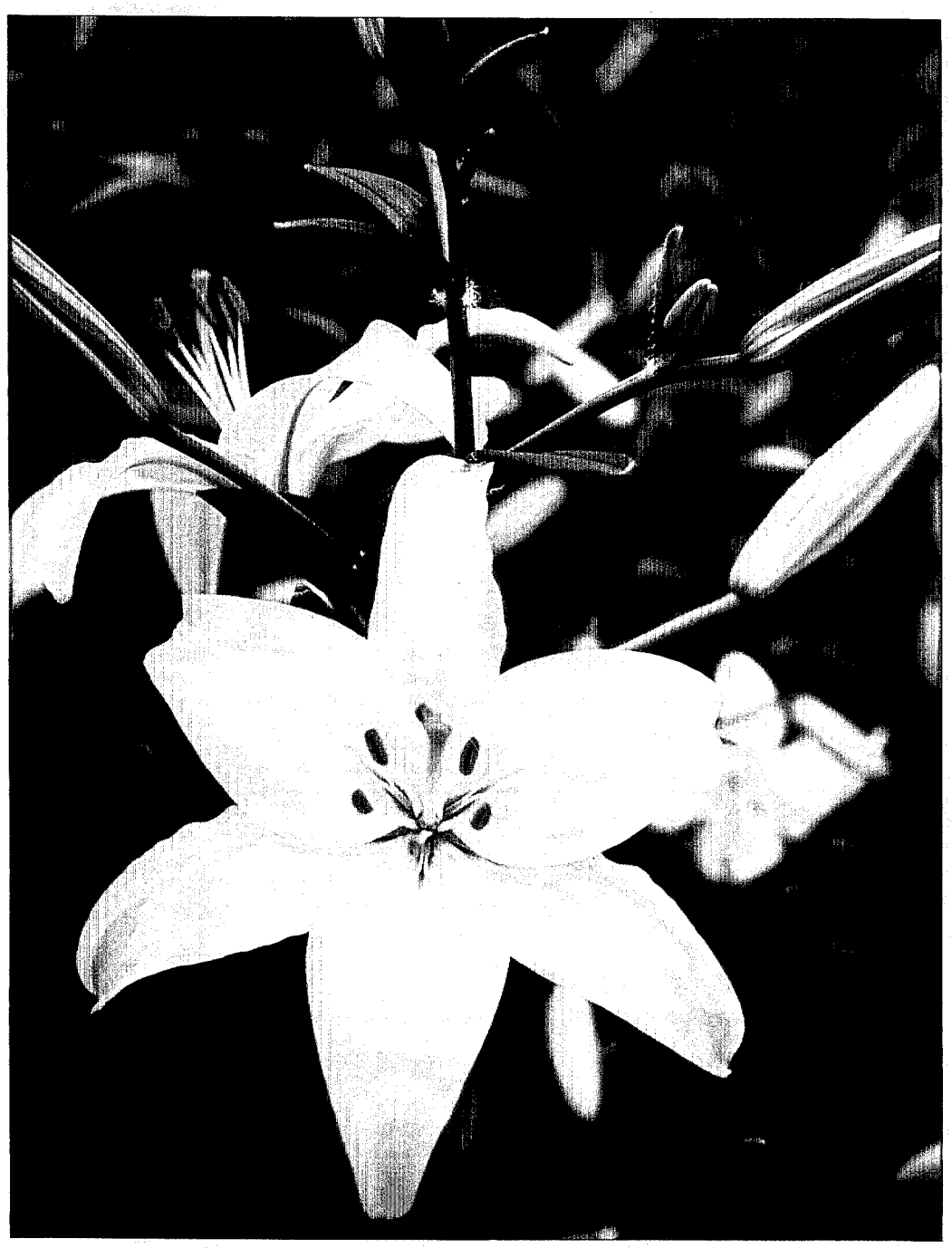

* * * * *